United States Patent [19]
Ikeda et al.

[11] 4,360,406
[45] Nov. 23, 1982

[54] PROCESS FOR THE PREPARATION OF TERTIARY BUTYL ALCOHOL

[75] Inventors: Minoru Ikeda, Hiroshima; Kazuya Okada, Otake; Hiroshi Matsumura, Sayama; Takeichi Tachihata, Hiroshima, all of Japan

[73] Assignee: Mitsubishi Rayon Co., Ltd., Tokyo, Japan

[21] Appl. No.: 282,163

[22] Filed: Jul. 10, 1981

Related U.S. Application Data

[63] Continuation-in-part of Ser. No. 91,246, Nov. 2, 1979, abandoned.

[30] Foreign Application Priority Data

Nov. 6, 1978 [JP] Japan .................. 53-136538

[51] Int. Cl.$^3$ ............................ B01D 3/34; B01D 3/40
[52] U.S. Cl. ................................... 203/32; 203/76; 203/96; 203/97; 568/917
[58] Field of Search ............... 568/840, 895, 913, 917; 203/95-97, 76, 77, 83, 85, 28, 29, 31, 32, 39

[56] References Cited

U.S. PATENT DOCUMENTS 2,663,679 12/1953 Drout .................................. 203/96
4,011,272 3/1977 Matsuzawa et al. ................ 568/913

*Primary Examiner*—Frank Sever
*Attorney, Agent, or Firm*—Cushman, Darby & Cushman

[57] ABSTRACT

Provided is a process for preparing tertiary butyl alcohol from isobutylene comprising reacting isobutylene or a hydrocarbon mixture containing isobutylene with an aqueous solution of an aliphatic carboxylic acid having from 1 to 6 carbon atoms in the presence of a solid, acidic ion-exchange resin as catalyst, to produce an aqueous reaction mixture of a major amount of tertiary butyl alcohol and a minor amount of the tertiary butyl ester of the carboxylic acid comprising the improved steps of:

(1) subjecting said reaction mixture to distillation to remove unreacted isobutylene or hydrocarbon mixture therefrom;
(2) supplying the treated reaction mixture of step (1) to a distillation column and passing water from the top to the bottom of said distillation column to remove said tertiary butyl ester of the carboxylic acid, wherein the amount of water used for removing the ester in step (2) is less than the sum of the amount of water used for converting said isobutylene into tertiary butyl alcohol and the amount of water contained in the tertiary butyl alcohol product;
(3) contacting the distillate obtained from the ester removal column with a strongly acidic ion-exchange resin to hydrolyze said tertiary butyl ester in the distillate; and thereafter
(4) returning said hydrolyzed liquid to the distillation column of step (2).

4 Claims, 1 Drawing Figure

PROCESS FOR THE PREPARATION OF TERTIARY BUTYL ALCOHOL

CROSS-REFERENCE TO RELATED APPLICATIONS

This is a continuation-in-part of our earlier application Ser. No. 91,246 filed Nov. 2, 1979, now abandoned, the disclosure of which is hereby incorporated by reference.

BACKGROUND OF THE INVENTION

The present invention relates to a process for the preparation of tertiary butyl alcohol from isobutylene or hydrocarbon mixture containing isobutylene while maintaining high purity, high yield and high productivity.

There are various methods for producing tertiary butyl alcohol by the hydration of isobutylene. For instance, there is one method which employs sulfuric acid as a catalyst. According to this method no particular device is required to enhance the contact efficiency between the reaction material and the catalyst, because the catalyst itself is uniformly dissolved in the reactants. With this method, however, if unreacted isobutylene or the hydrocarbon mixture containing the unreacted isobutylene were removed by distillation from the reaction product in which the catalyst is dissolved, the equilibrium reaction permits the tertiary butyl alcohol to be simultaneously dehydrated. Thus using this procedure it is necessary to neutralize the sulfuric acid catalyst in the reaction mixture prior to recovering and refining the tertiary butyl alcohol. This means that the catalyst cannot be re-used in the process and thus economically disadvantageous.

To cope with this disadvantage various methods have been proposed which use solid catalysts that are insoluble in the reactants and which permit the solid catalyst to be present only in the reactor. As an example it is known that acidic ion exchange resins are effective as a solid catalyst, however when such a solid catalyst is used, the reaction does not proceed efficiently unless isobutylene and water are brought into intimate contact with the solid catalyst. In particular, when the hydrocarbon mixture which serves as a source of isobutylene is reacted under an elevated pressure in the liquid phase, the reaction liquid forms two phases consisting essentially of water and those hydrocarbons insoluble in the water. This phase formation makes it quite difficult to raise the contact efficiency with respect to a solid catalyst such as an ion exchange resin. Although various attempts for enhancing the contact efficiency have been reported, a satisfactory means has yet to be found.

However, U.S. Pat. No. 4,011,272 describes that when isobutylene or a hydrocarbon mixture containing isobutylene is reacted with an aqueous solution of an aliphatic carboxylic acid in the presence of an acidic ion exchange resin under conditions such that the reaction liquid forms a homogeneous solution, the catalytic efficiency between the catalyst and the reaction liquid is increased enabling the hydration reaction rate to be substantially increased. According to the process described it is possible not only to form tertiary butyl alcohol efficienctly but also to recover and refine the tertiary butyl alcohol produced thereby maintaining high purity and high yield. The sole defect inherent in the system disclosed in U.S. Pat. No. 4,011,272, however, is the formation of undesirable tertiary butyl esters of the aliphatic carboxylic acid as a by-product in small amounts during the course of the reaction. The problem is that it is difficult to separate tertiary butyl alcohol and its tertiary butyl ester by conventional distillation. Therefore, the tertiary butyl alcohol and the tertiary butyl ester in the entire amount are separated by distillation from the carboxylic acid aqueous solution and are both hydrolyzed. It is at this point that the hydrolyzed liquid must be separated into an aqueous solution of the carboxylic acid and tertiary butyl alcohol, and this requires an increased amount of heat in the form of steam.

SUMMARY OF THE INVENTION

In order to dispense with the difficult and energy-intensive isolation and removal of the unwanted tertiary butyl ester, the present inventors have conducted intensive studies and have unexpectedly discovered the fact that the unwanted tertiary butyl ester can be easily separated by supply water to the top of the distilling column for removing the tertiary butyl ester and have thus accomplished the present invention as herein described.

In overview, the present invention provides a process for preparing tertiary butyl alcohol from isobutylene, including reacting isobutylene, or a hydrocarbon mixture containing isobutylene, with an aqueous solution of aliphatic carboxylic acid having from 1 to 6 carbon atoms in the presence of acidic ion exchanger to product tertiary butyl alcohol together with an impurity amount of the ester thereof, the improvement of removing the unwanted tertiary butyl ester characterized by supplying water to the top of the distilling column for removing the tertiary butyl ester of the carboxylic acid after removing any unreacted isobutylene or the hydrocarbon mixture. Additionally, the separated tertiary butyl ester is hydrolyzed using a strong acidic ion-exchanger and the reaction product is recycled to the ester-removing distilling column. These and other features of the present invention will now be described in more detail below.

DETAILED DESCRIPTION OF THE PREFERRED EMBODIMENTS

Figure 1:
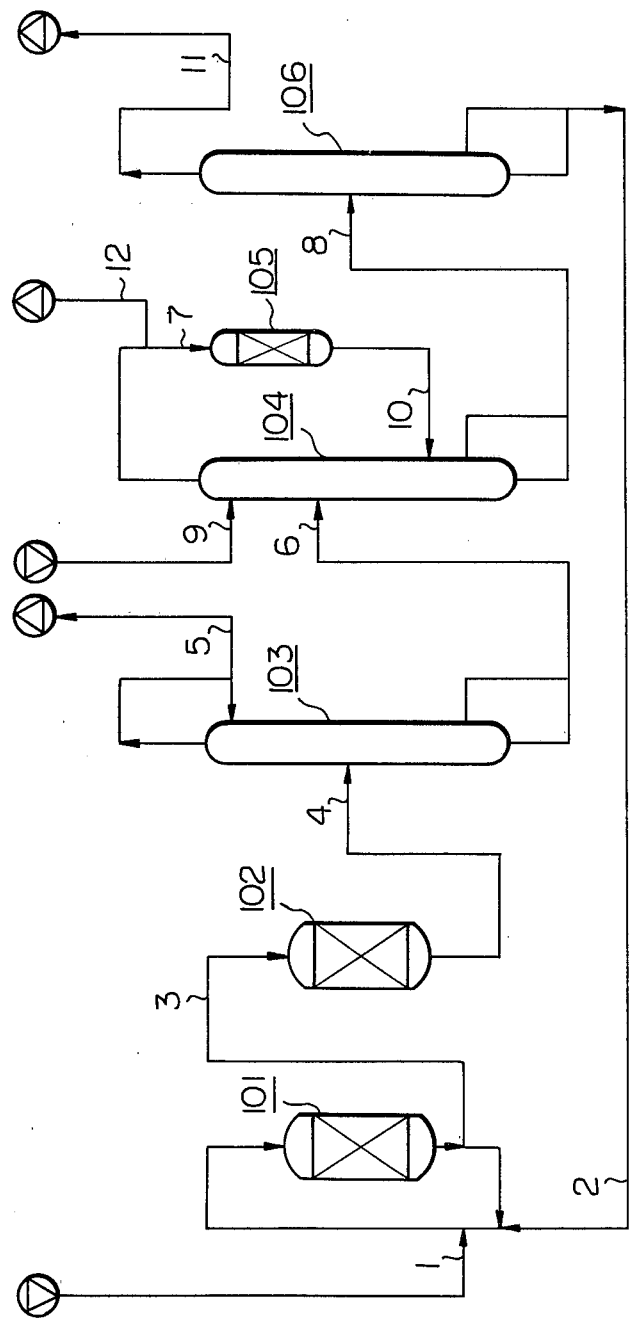
FIG. 1 shows an example of a flow sheet illustrating the steps for producing the tertiary butyl alcohol according to the process of the present invention.

The process of the present invention employs aliphatic carboxylic acids having 1 to 6 carbon atoms because they are desirable for separating the tertiary butyl ester of carboxylic acid. Of these acids, acetic acid or propionic acid are most preferred from the standpoint of separation, stability and cost. The molar ratio of carboxylic acid to water is preferably in the range of 0.3 to 5.0 for optimum results.

It is important that the reaction conditions are selected such that the reaction liquid becomes a homogeneous solution. The reaction temperature may range from 20° to 80° C. and is preferably between 40° and 80° C. The reaction can be carried out under atmospheric pressure or elevated pressure, and usually it is desirable to operate the process at a pressure which liquefies the hydrocarbon mixture.

A wide range of generally known acidic ion-exchange resins can be used as described for instance, in U.S. Pat. No. 4,011,272, mentioned above. The preferred resins are the acidic ion-exchange resins of the sulfonic acid type cation-exchange resins and are preferably porous. More specifically such resins may be the polystyrene-type cation exchange resins, for example Amberlite IR-118, IR-120 or IR-200 or Amberlyst-15 (Rohm & Haas Co.) or Diaion PK-208, PK-228 or SK-102 (produced by Mitsubishi Kasei Co.) or Dow-50 (Dow Chemical Co.).

After the hydration reaction, the hydrocarbon mixture containing the unreacted isobutylene is separated by conventional distillation procedures from the reaction liquid and the solution which consists of tertiary butyl alcohol, the tertiary butyl ester, water and carboxylic acid, hereinafter referred to as t-butanol-ester solution, is obtained.

It is difficult to separate tertiary butyl ester from the t-butanol-ester solution by conventional distillation. Unexpectedly, however, by supplying only the water which is the raw material of hydration to the top of the distilling column for removing the tertiary butyl ester, the ester can be easily separated from the tertiary butyl alcohol product. The distilling column is operated under atmospheric pressure or reduced pressure and at head temperatures ranging from 50° to 90° C., preferably 70° to 80° C., depending upon the pressure employed.

A highly desirable feature of the process of the present invention is that the amount of water required may be less than the sum of the amount which is converted into the product and the amount distilled off accompanying the product. The distillate which contains the tertiary butyl ester impurity is then hydrolyzed with a strong acidic ion-exchanger and the reaction product recycled to the ester-removing column. The hydrolysis reaction can be carried out at a rate of conversion greater than 95% without adding additional water.

After hydrolysis, the reaction liquid is preferably supplied to a suitable stage in the stripping section of the ester-removing column. The bottoms of the ester-removing column are transferred to the distilling column for separating into tertiary butyl alcohol as the product distillate and the carboxylic acid aqueous solution as bottoms which can be returned to the hydration reactor.

Thus the process of the present invention is simple and rational as compared with the conventional processes, and makes it possible to prepare tertiary butyl alcohol while maintaining high yield and at a reduced cost.

DETAILED DESCRIPTION OF THE DRAWING

The process of the present invention is further explained below with reference to the drawing. Reference numerals 101 and 102 represent the first hydration reactor and the second hydration reactor, respectively, filled with an acidic ion-exchanger. The first hydration reactor is a complete mixing type and the second hydration reactor is of the piston flow type. The first hydration reactor 101 is supplied with a hydrocarbon mixture containing isobutylene through line 1 and carboxylic acid aqueous solution through line 2. The first reactor 101 is preferably operated under the condition such that the liquid discharged from the reactor is homogeneous.

The liquid discharged from the second reactor 102 is fed through line 4 to a distilling column 103 for separating hydrocarbons, where the hydrocarbon mixture containing unreacted isobutylene is taken out through line 5. Reference numeral 104 represents a distilling column for removing tertiary butyl ester from the liquid of line 6. Water is supplied to distilling column 104 through line 9. The distillate taken out through line 7 is sent to a hydrolysis reactor 105 filled with an acidic ion-exchange resin. The reaction product is returned to the ester-removing column through line 10. Line 12 represents vent gas from the condenser of column 104, which consists primarily of isobutylene formed in the hydrolysis reactor. The bottoms from column 104 are sent to distilling distillation column 106 through line 8. The distillate which is an aqueous solution of tertiary butyl alcohol is removed through line 11 and the carboxylic acid aqueous solution is taken out through line 2 and may be recycled to the first hydration reactor 101. The tertiary butyl alcohol product may be separated from the water according to conventional procedures.

Having generally described the present invention in flow sheet operation, a more complete understanding will be obtained by reference to the following working examples, which are included for purposes of illustration only and are not intended to limit the process of the invention.

EXAMPLE 1

This is an example of a process for preparing tertiary butyl alcohol in accordance with the present invention and following the flow sheet illustrated in the accompanying drawing. Table 1 shows the composition of the hydrocarbon mixture used as one of the reactants. This hydrocarbon mixture was supplied through line 1 at a rate of 100 mol/hr. As the other reactant an aqueous solution consisting of acetic acid and water in a molar ratio of 1 to 2 was supplied to the first hydration reactor through line 2 at a rate of 176 mol/hr. The first hydration reactor and the second hydration reactor were previously charged with 7 liters and 6 liters, respectively, of a sulfonic acid-type cation exchange resin. The first hydration was carried out at 77° C., 10 Kg/cm$^2$ and the second hydration at 70° C., 10 Kg/cm$^2$. Distillation column 103 was a conventional sieve-tray column. The distillate composition of line 5 is shown in Table 1, and the bottoms composition of line 6 is shown in Table 2.

The isobutylene conversion was 92% and the selectivity for tertiary butyl acetate was 4.4%. The dimer of isobutylene and the reaction products from n-butenes were present in trace amounts. Column 104 for separating the tertiary butyl acetate impurity had 35 stages. Water was supplied from the top of the column at a rate of 72 mol/hr, the liquid from line 6 was supplied to the column at the fifth stage from the top, and the hydrolyzed liquid from the hydrolysis reactor was supplied to the column at the twenty-fifth stage from the top. The distillate was taken out at the rate of 43 mol/hr. The hydrolysis reactor was previously charged with the same sulfonic acid-type ion exchange resin as in the hydration reactors, and recycled the liquid of line 7 to the ester-removing column after completing the hydrolysis reaction. The rate of hydrolysis was greater than 95%. As a result, the amount of the tertiary butyl acetate in the product obtained through line 11 significantly decreased to only 0.17 mole %. The compositions of the reaction mixtures and distillates of lines 7 and 11 are shown in Table 2.

TABLE 1

| Component | Line Number | |
|---|---|---|
| | 1 | 5 |
| Isobutylene | 45.0 mol % | 6.1 mol % |
| 1-Butene | 26.0 | 44.4 |
| 2-Butene | 15.0 | 25.6 |
| Butane | 14.0 | 23.9 |

The bottoms from distillation column 104 were subjected to an additional distillation step in column 106 and an extremely pure solution of t-butyl alcohol (56%) in water (43.8%) free of acetic acid was obtained via line 11 while the recovered acetic acid solution was recycled via line 2 and re-used in the series connected hydration reactors.

TABLE 2

| Component | Line Number | | |
|---|---|---|---|
| | 6 | 7 | 11 |
| Tertiary butyl alcohol | 22.6 mol % | 44.0 mol % | 56.0 mol % |
| Tertiary butyl acetate | 1.04 | 4.15 | 0.17 |
| Water | 44.1 | 51.9 | 43.8 |
| Acetic acid | 32.3 | 0 | 0 |

COMPARATIVE EXAMPLE A

As a means of comparison in place of the ester-removing column 104 used in Example 1 which is according to the invention, a conventional distillation column for refluxing the distillate was employed in place of distillation column 104. As a modification, water was added to the distillate (via line 7', not shown in the drawing but discussed below) and was returned to column 104 after being subjected to hydrolysis conditions. The hydrolysis rate was 95%. The results under the operating conditions of the amount of the distillate of column 104 was 6 mol/hr and the reflux was 10, are shown in Table 3 in terms of composition of line 6, 7' and 11' (in which 11' corresponds to line 11 of the drawing). According to this modified arrangement the amount of the steam required for heating the reboiler used for column 104 was 1.4 times that of Example 1 and the amount of the teritary butyl acetate impurity in the product is 2.4 times that of Example 1.

TABLE 3

| Component | Line Number | | |
|---|---|---|---|
| | 6 | 7' | 11' |
| Tertiary butyl alcohol | 29.3 mol % | 59.5 mol % | 56.0 mol % |
| Tertiary butyl acetate | 1.35 | 21.2 | 0.4 |
| Water | 37.4 | 19.0 | 43.6 |
| Acetic acid | 32.0 | 0 | 0 |

COMPARATIVE EXAMPLE B

Example 1 was repeated but this time a distillation column was used, from which the distillate formed two liquid phases when it was mixed with water rather than the ester removal column. The lower phase was returned to the top of the column as reflux and the upper phase was subjected to the hydrolysis reaction. The rate of hydrolysis was 94%. However, under the various distillation conditions employed the concentration of the ester impurity in the product could not be decreased in comparison with that of Example 1.

COMPARATIVE EXAMPLE C

In this example the water used for separating the teritary butyl ester in Example 1 was replaced with a carboxylic acid aqueous solution, however the hydrolysis rate was only 90%.

DISCUSSION OF THE RESULTS

As used in this specification and in the appended claims the expression "the amount of water is less than the sum of the amount of water used for converting the isobutylene into tertiary butyl alcohol and the amount of water contained in the tertiary butyl alcohol product" means the sum of the mole amount of water in line 11. This is because that the amount of water used for converting isobutylene into TBA equals the mole amount of TBA, due to the conversion needs one mole of water for one mole of TBA production. When "the sum of the amounts of water" is more than the amount of water supplied to the top of the column via line 9, then the amount of water in the distilling column is less than "the sum of the amounts of water" as is defined.

The mole % of water in TBA product (line 11) becomes little more than 35 mole % because of azeotrope of $H_2O$ 35 mole % and TBA 65 mole %.

Example 1 below contrasted with Comparative Example A:

Flow Sheet of Ex. 1

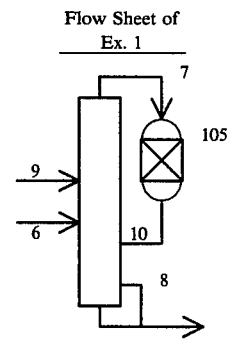

Flow Sheet of Comparative Ex. A

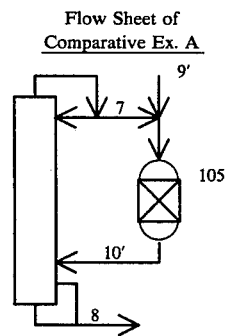

The flow rates of each of the two Examples illustrated above are shown below:

| Line No. | Example 1 | | | | Comparative Example A | | | |
|---|---|---|---|---|---|---|---|---|
| | Total mol/hr | TBA mol/hr | TBAC mol/hr | H$_2$O mol/hr | Total mol/hr | TBA mol/hr | TBAC mol/hr | H$_2$O mol/hr |
| 6 | 175 | 39.6 | 1.82 | 77.2 | 135 | 39.6 | 1.82 | 50.5 |
| 7 (7') | 43 | 18.9 | 1.78 | 22.3 | 6 | 3.57 | 1.27 | 1.14 |
| 9 (9') | 72 | 0 | 0 | 72 | 72 | 0 | 0 | 72 |
| 11 (11') | 72.3 | 40.5 | 0.12 | 31.6 | 72.3 | 40.5 | 0.29 | 31.5 |

Thus it will be seen that in Example 1, the amount of water supplied to the top via line 9 is 72 mol/hr and "the sum of amounts of water" is 72.1 (that is 40.5+31.6) mol/hr, then the former is less than the latter.

The data displayed above is calculated from the data shown in the Example 1 and Comparative Example A. In Comparative Example A, the same amount of water was added into the hydrolysis reactor 105 via line 9' in place of the top of the column in Example 1. Even though the same amount of water was added and the reflux ratio was 10, which is very high—the efficiency for removing the tertiary butyl ester of the carboxylic acid (TBAC which is by-product) is very poor compared with that of Example 1 (2.4 times impurity). Thus comparative Example A does not give a comparison concerning the amount of water added via line 9 or 9', but rather the position of adding the water.

It is known in the art (c.f. U.S. Pat. No. 2,663,679) that the amount of water added to the top of the column should be a considerable amount of extracting agent (i.e., water) in order to remove the by-product completely. In such an arrangement, at least a part of separated water from the product must be discarded. In the process of the present invention, however, the separated water contains carboxylic acid, and therefore it cannot be thrown away for economic and environmental reasons.

We claim:

1. In a process for preparing tertiary butyl alcohol from isobutylene comprising reacting isobutylene or a hydrocarbon mixture containing isobutylene with an aqueous solution of an aliphatic carboxylic acid having from 1 to 6 carbon atoms in the presence of a solid, acidic ion-exchange resin as a catalyst, to produce an aqueous reaction mixture of a major amount of tertiary butyl alcohol and a minor amount of the tertiary butyl ester of the carboxylic acid, the improvement comprising the steps of:
(1) subjecting said reaction mixture to distillation to remove unreacted isobutylene or hydrocarbon mixture therefrom;
(2) supplying the treated reaction mixture of step (1) to a distillation column and passing water from the top to the bottom of said distillation column to remove said tertiary butyl ester of the carboxylic acid, wherein the amount of water used for removing the ester in step (2) is less than the sum of the amount of water used for converting said isobutylene into tertiary butyl alcohol and the amount of water contained in the tertiary butyl alcohol product;
(3) contacting the distillate obtained from the ester removal column with a strongly acidic ion-exchange resin to hydrolyze said tertiary butyl ester in the distillate; and thereafter
(4) returning said hydrolyzed liquid to the distillation column of step (2).

2. The process as claimed in claim 1 wherein the molar ratio of the aliphatic carboxylic acid to water in the aqueous carboxylic acid solution is in the range of about 0.3 to about 5.0.

3. The process as claimed in claim 1 wherein the reaction mixture treated in step (1) is a homogeneous solution.

4. A process for preparing tertiary butyl alcohol substantially completely free of tertiary butyl ester impurities, said process comprising:
(a) reacting isobutylene or a hydrocarbon mixture containing isobutylene with an aqueous solution of an aliphatic carboxylic acid having from 1 to 6 carbon atoms in the presence of a solid, acidic ion-exchange resin at a temperature of about 20° C. to about 80° C. to produce a homogeneous solution reaction mixture comprising a major amount of tertiary butyl alcohol, a minor amount of the tertiary butyl ester of the carboxylic acid, unreacted isobutylene and water,
wherein the molar ratio of said aliphatic carboxylic acid to water in said aqueous reactant solution is in the range of about 0.3 to about 5.0,
(b) distilling the homogenous reaction mixture of step (a) to remove unreacted isobutylene or hydrocarbon mixture therefrom;
(c) supplying the isobutylene-free aqueous solution of step (b) to an ester removal column and passing water from the top of said column to the bottom thereof subjecting said isobutylene-free aqueous solution to distillation conditions of about 50° C. to about 90° C. at the head temperature and removing said tertiary butyl ester of the carboxylic acid as the distillate, wherein the amount of water supplied to the top of the column is less than the sum of (1) the amount of water used for converting the isobutylene into tertiary butyl alcohol, plus (2) the amount of water contained in the tertiary butyl alcohol product;
(d) hydrolyzing said tertiary butyl ester of the carboxylic acid removed in step (c) by contacting with a strongly acidic ion-exchange resin and returning the hydrolyzed liquid to the ester removal column of step (c); and
(e) distilling the bottom portion of the liquid of step (c) and recovering an aqueous solution of tertiary butyl alcohol.

* * * * *